US00PP08726P

United States Patent [19]

Schumann

[11] Patent Number: Plant 8,726

[45] Date of Patent: May 10, 1994

[54] GERANIUM PLANT NAMED FISCRID

[75] Inventor: Ingeborg Schumann, Albstadt, Fed. Rep. of Germany

[73] Assignee: Florfis AG, Binningen, Switzerland

[21] Appl. No.: 94,326

[22] Filed: Jul. 21, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium named Fiscrid, particularly characterized by its large brilliant red flowers, good heat tolerance, foliage with slight zonation, and medium to vigorous growth.

1 Drawing Sheet

The present invention comprises a new and distinct cultivar of geranium, botanically known as *Pelargonium zonale* l'hert, and hereinafter referred to by the cultivar name Fiscrid.

Fiscrid is a product of planned breeding program which had the objective of creating new geranium cultivars with bright red flower color, medium green foliage and good growth characteristics.

Fiscrid was originated from a hybridization made by the inventor Ingeborg Schumann in a controlled breeding program in Galdar, Gran Canaria, Spain in 1987. The female parent was an inbred seedling of Dresden Doll, pink, characterized by single light pink flowers with purple eyes, foliage with weak zonation and medium growth habit. The male parent of Fiscrid was EP 387, a dark red variety with purple eyes, foliage without zonation and compact growth habit.

Fiscrid was discovered and selected as one flowering plant within the progeny of the stated cross by Ingeborg Schumann in 1988 in a controlled environment in Galdar, Gran Canaria, Spain.

The first act of asexual reproduction of Fiscrid was accomplished when vegetative cuttings were taken from the initial selection in February 1989 in a controlled environment in Galdar, Gran Canaria, Spain, by, or under the supervision of, Ingeborg Schumann.

Horticultural examination of plants grown from these cuttings initiated in May 1989 in Hillscheid, Federal Republic of Germany, and continuing thereafter, has demonstrated that the combination of characteristics as herein disclosed for Fiscrid are firmly fixed and are retained through successive generations of asexual reproduction.

Fiscrid has not been observed under all possible envionmental conditions. The phenotype may vary significantly with variations in environment such as temperature, light intensity and day length without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristic of Fiscrid, which in combination distinguish this geranium as a new and distinct cultivar:

1. Brilliant red flower color, without tendency to fading or bluing
2. Large semi-double flowers 3. Comparatively good heat tolerance for a red flowering variety
4. Medium to broad plant habit
5. Medium green foliage with slight zonation Of the many commercial cultivars known to the present inventor, the most similar incomparison to Fiscrid is Robe. Reference is made to attached Chart A which compares certain characteristics of Fiscrid to those same characteristics of Robe. In general comparison to Robe, Fiscrid has a somewhat lighter flower color, more vigorous growth, and no markings on the upper petals.

The accompanying color photographic drawing shows typical flower and foliage characteristics of Fiscrid, with colors being as true as possible with illustrations of this type.

In the following description color references are made to the Royal Horticultural Society Colour Chart. The color values were determined indoors from plants grown in a greenhouse in May at Hillscheid, Federal Republic of Germany.

Classification:

*Botanical.*—A hybrid of the species *Pelargonium zonale* l'Hert.

*Commercial.*—Zonal geranium, cv., Fiscrid.

INFLORESCENCE

A. Umbel:

*Shape.*—Semi-spherical.
*Average diameter.*—115 mm.
*Average depth.*—55 mm.
*Peduncle length.*—180 mm.
*Pedicel length.*—35 mm.
*Pedicel color.*—Light to dark red.
*Number of flowers per umbel.*—40–50.

B. Corolla:

*Average diameter.*—48 mm.
*Form.*—Semi-double.
*Average number of petals.*—9–11.
*Average number of petaloids.*—2–4.
*Color (general tonality from a distance of three meters).*—Red.
*Color of upper petals.*—44 A.
*Color of lower petals.*—46 C.
*Color of lower surface of petals.*—46 C-D.
*Color of sepals.*—Mainly dark red.
*Number of sepals.*—5–6.

C. Bud:

*Shape.*—Round to elliptic.

*Color (adaxial).*—Green, with little anthocyanin at the base.

*Color (abaxial).*—Bluish pink to red.

D. Reproductive organs:

*Androecium.*—4–6 fertile anthers, orange pollen.

*Gynoecium.*—5–6 lobed stigma, dark red style and stigma.

E. Spring flowering response period: In Hillscheid, Federal Republic of Germany, in 1993 plants had on average 0.7 flowers opened 10 weeks after planting of unrooted cuttings.

F. Outdoor flower production: The flower count in 1992 in Hillscheid, Federal Republic of Germany was between 25 and 30 flowers per plant for May through August observation period.

G. Durability: Good shatter resistance.

PLANT

A. Foliage:

*Form.*—Kidney-shaped.

*Margin.*—Bicrenate.

*Color of upper surface.*—Medium green, approximately 137B.

*Color of zonation.*—Brown, approximately 166 A.

*Tolerance of botrytis.*—Average.

B. General appearance and form:

*Internode length.*—20–30 mm.

*Branching pattern.*—2.5 branches per plant per week.

*Height* (12 week old plants).—15 cm.

CHART A

| | FISCRID | ROBE |
|---|---|---|
| Color of upper petals | 44 A | 46 B-C |
| Color of lower petals | 46 C | 46 C |
| Markings | None | orange eyes on upper petals |
| Plant Height | 15 cm | 11 cm |
| Number of flowers per plant | 0.7 | 1.3 |

I claim:

1. A new and distinct cultivar of geranium plant named Fiscrid, as illustrated and described.

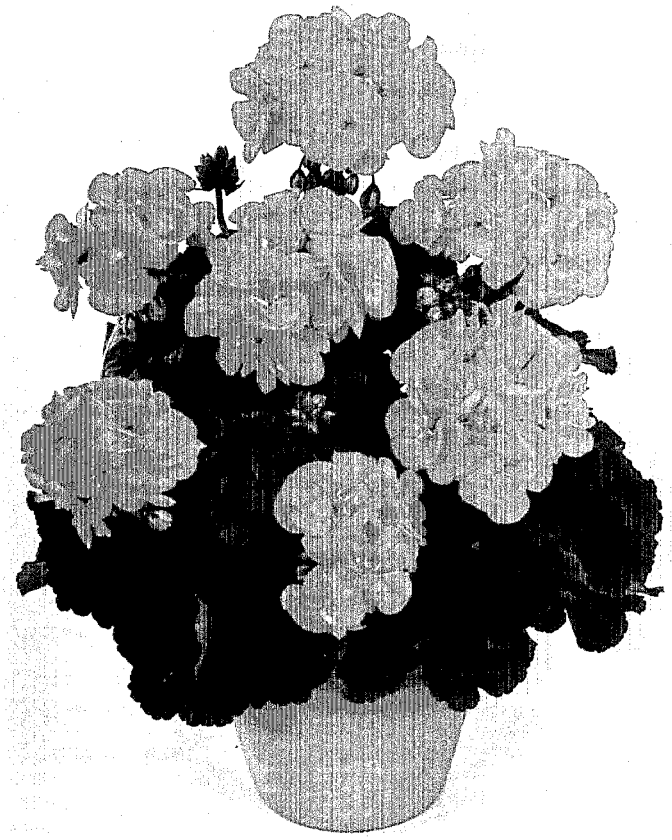

* * * * *